United States Patent
Egwu

(10) Patent No.: US 10,859,368 B2
(45) Date of Patent: Dec. 8, 2020

(54) SMART LAWN SENSOR ADAPTED TO MONITOR LAWN HEIGHT AND SYSTEM OF PROVIDING LAWN CARE

(71) Applicant: Wilkinson Egwu, Woodstock, GA (US)

(72) Inventor: Wilkinson Egwu, Woodstock, GA (US)

( * ) Notice: Subject to any disclaimer, the term of this patent is extended or adjusted under 35 U.S.C. 154(b) by 0 days.

(21) Appl. No.: 16/288,482

(22) Filed: Feb. 28, 2019

(65) Prior Publication Data

US 2020/0149869 A1 May 14, 2020

Related U.S. Application Data

(60) Provisional application No. 62/767,125, filed on Nov. 14, 2018.

(51) Int. Cl.
| | | |
|---|---|---|
| G08B 21/00 | (2006.01) | |
| G01B 11/02 | (2006.01) | |
| G08B 21/18 | (2006.01) | |
| G01L 19/00 | (2006.01) | |
| G01N 33/24 | (2006.01) | |

(52) U.S. Cl.
CPC .......... *G01B 11/02* (2013.01); *G01L 19/0092* (2013.01); *G01N 33/246* (2013.01); *G08B 21/182* (2013.01)

(58) Field of Classification Search
CPC .. G01B 11/02; G01L 19/0092; G01N 33/246; G08B 21/182
See application file for complete search history.

(56) References Cited

U.S. PATENT DOCUMENTS

| | | | | |
|---|---|---|---|---|
| 4,777,785 A * | 10/1988 | Rafaels | ................ | A01D 34/008 56/10.2 A |
| 5,528,888 A * | 6/1996 | Miyamoto | ........... | A01B 69/008 56/10.2 F |
| 7,613,552 B2 * | 11/2009 | Bernini | ................ | A01D 34/008 180/168 |
| 8,027,761 B1 * | 9/2011 | Nelson | .................... | G01S 1/805 701/23 |
| 8,275,506 B1 * | 9/2012 | Bishel | ..................... | G01S 13/87 701/25 |
| 10,021,830 B2 * | 7/2018 | Doughty | ................. | A01D 34/81 |
| 10,034,421 B2 * | 7/2018 | Doughty | .............. | A01D 34/008 |
| 10,100,968 B1 * | 10/2018 | Chow | ...................... | B25J 18/06 |
| 10,705,533 B1 * | 7/2020 | Bishel | .................. | G05D 1/0231 |
| 2010/0050584 A1 * | 3/2010 | Whitehead | ........... | A01D 34/416 56/10.2 A |
| 2013/0047565 A1 * | 2/2013 | Shida | .................... | G05B 19/182 56/10.2 H |
| 2014/0266684 A1 * | 9/2014 | Poder | .................... | G08B 25/001 340/521 |
| 2015/0096276 A1 * | 4/2015 | Park | ..................... | A01D 34/008 56/10.2 A |

(Continued)

*Primary Examiner* — Quang Pham
(74) *Attorney, Agent, or Firm* — Dunlap Bennett & Ludwig, PLLC

(57) ABSTRACT

A smart lawn sensor is provided. The smart lawn sensor provides a grass height sensor adapted to determine the elevation of adjacent grass. The smart lawn sensor provides control circuitry operatively associated with the grass height sensor. The control circuitry may be programmed to set thresholds for the determined grass height so that the control circuitry sends notifications to one or more remote computing devices if the set thresholds are met or exceeded.

6 Claims, 4 Drawing Sheets

(56) References Cited

U.S. PATENT DOCUMENTS

| | | | |
|---|---|---|---|
| 2016/0157422 A1* | 6/2016 | Kohler | A01D 34/008 |
| | | | 700/275 |
| 2016/0252615 A1* | 9/2016 | O'Sullivan | G01S 15/88 |
| | | | 367/99 |
| 2017/0367257 A1* | 12/2017 | Cmich | A01D 34/008 |
| 2018/0132469 A1* | 5/2018 | Frudakis | A01M 1/226 |
| 2019/0283533 A1* | 9/2019 | Lombrozo | G01S 7/4813 |
| 2019/0313589 A1* | 10/2019 | Johnson | A01C 23/023 |

* cited by examiner

SMART LAWN SENSOR ADAPTED TO MONITOR LAWN HEIGHT AND SYSTEM OF PROVIDING LAWN CARE

CROSS-REFERENCE TO RELATED APPLICATION

This application claims the benefit of priority of U.S. provisional application No. 62/767,125, filed 14 Nov. 2018, the contents of which are herein incorporated by reference.

BACKGROUND OF THE INVENTION

The present invention relates to lawn care and, more particularly, a smart lawn sensor and a system of providing lawn care.

Mowing a lawn is time consuming and tedious, but weekly professional lawn services can be expensive. Professional lawn service providers also tend to be inflexible in terms of not mowing the lawn even when unnecessary; for instance, when the height of the grass hadn't increased significantly since the last cutting because of recent weather or seasonal conditions.

Unfortunately, there currently are no devices adapted to detect lawn height for the purpose of identifying when a lawn cutting is required, and as a corollary offering the capacity of scheduling only necessary lawn service work.

As can be seen, there is a need for a smart lawn sensor and a system of providing lawn care The present invention embodies one or more sensors adapted to both detect the height of grass and automatically communicate via software to a lawn service provider and or the lawn's owner so that the lawn only gets cut when necessary, saving time and money.

SUMMARY OF THE INVENTION

In one aspect of the present invention, a smart lawn sensor includes the following: a first housing having an upward-facing surface and a downward-facing surface; a grass height sensor disposed in the first housing so as to be operatively associated with a portion of the downward-facing surface, wherein the grass height sensor is configured to measure a first distance and a second distance between the downward-facing surface and a supporting surface and between the downward-facing surface and an upper elevation of plant life between the supporting surface and the downward-facing surface, respectively; a post extending from the downward-facing surface so as to connect the downward-facing surface to the supporting surface; and a control circuitry coupled to the grass height sensor, wherein the control circuitry is configured to determine a difference between said first and second distances.

In another aspect of the present invention, the smart lawn sensor includes the following: a first housing having an upward-facing surface and a downward-facing surface; a grass height sensor disposed in the first housing so as to be operatively associated with a portion of the downward-facing surface, wherein the grass height sensor is configured to measure a first distance and a second distance between the downward-facing surface and a supporting surface and between the downward-facing surface and an upper elevation of plant life between the supporting surface and the downward-facing surface, respectively, wherein the grass height sensor utilizes infrared imaging functionality to determine said first and second distances; a post extending from the downward-facing surface so as to connect the downward-facing surface to the supporting surface; a control circuitry coupled to the grass height sensor, wherein the control circuitry is configured to determine a difference between said first and second distances; and a moisture sensor integrated with a distal end of the post, so that the moisture sensor measures the moisture content of the supporting surface; a solar energy collector integrated with the upward-facing surface, wherein the solar energy collectors converts sunlight to electricity powering the control circuitry; and a temperature and pressure sensor housed in the first housing, where in the temperature and pressure sensor is configured to measure the ambient temperature and atmospheric pressure, wherein the control circuitry is configured to programmably set a predetermine threshold as a function of said difference, the moisture content and the ambient temperature and or the atmospheric pressure, wherein the control circuitry is configured to send an alert if the predetermine threshold is met or exceeded.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a smart lawn sensor that can be embodied in a system of providing lawn care. The smart lawn sensor provides a grass height sensor adapted to determine the elevation of adjacent grass. The smart lawn sensor provides control circuitry operatively associated with the grass height sensor. The control circuitry may be programmed to set thresholds for the determined grass height so that the control circuitry sends notifications to one or more remote computing devices if the set thresholds are met or exceeded.

Figure 1:
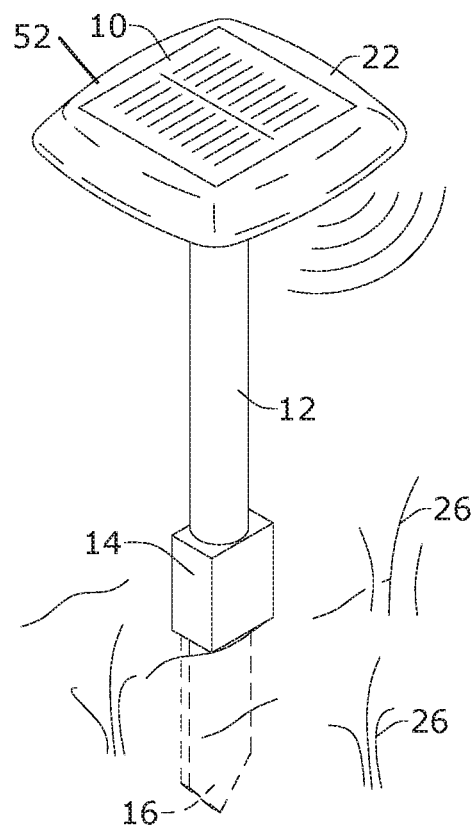
FIG. 1 is a perspective view of an exemplary embodiment of the present invention, shown in use.
Figure 2:
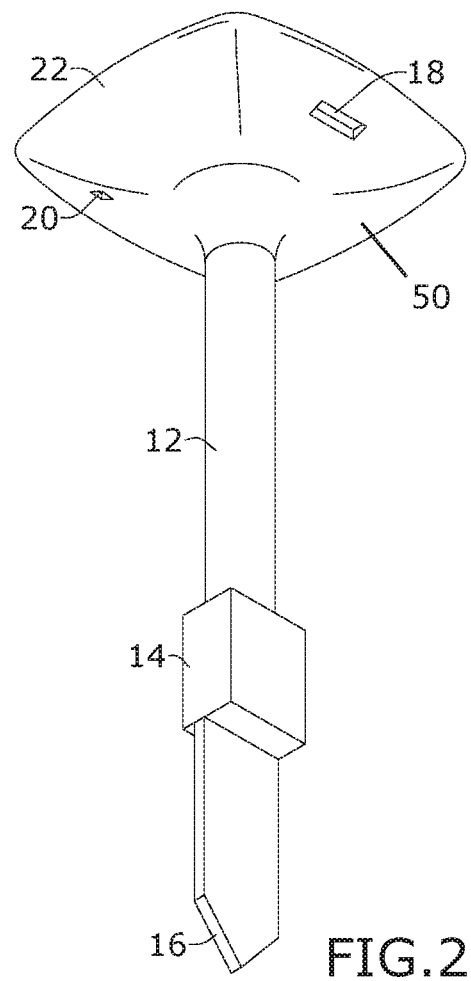
FIG. 2 is a bottom perspective view of an exemplary embodiment of the present invention.
Figure 3:
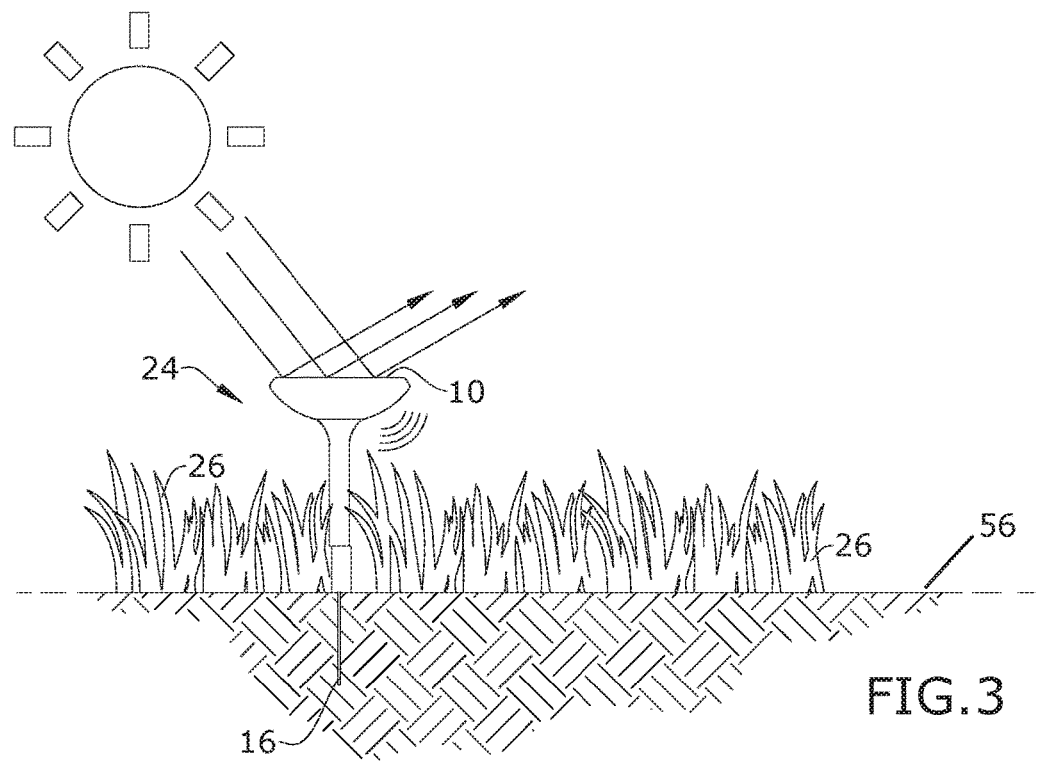
FIG. 3 is a schematic view of an exemplary embodiment of the present invention, illustrating solar energy capture.
Figure 4:
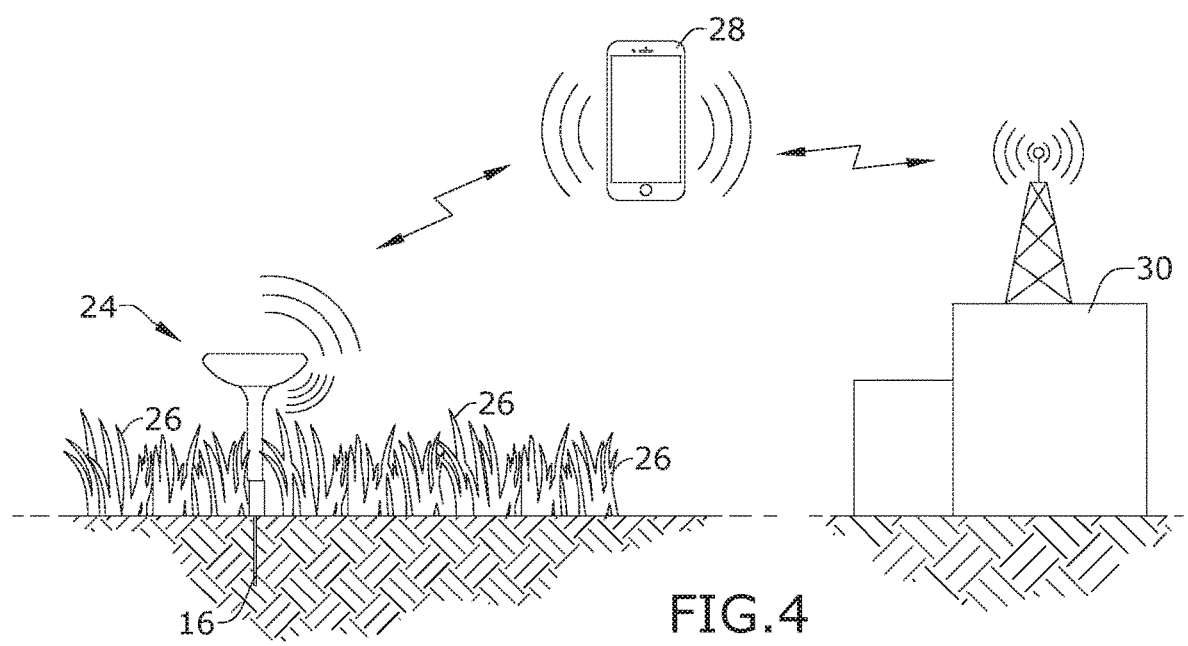
FIG. 4 is a schematic view of an exemplary embodiment of the present invention, illustrating a communication process.
Figure 5:
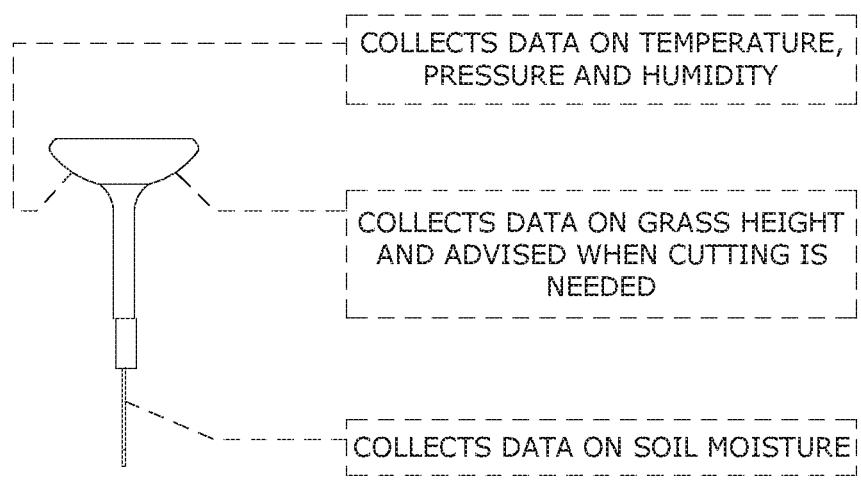
FIG. 5 is a schematic view of an exemplary embodiment of the present invention, illustrating an arrangement of a plurality of sensors.
Figure 6:
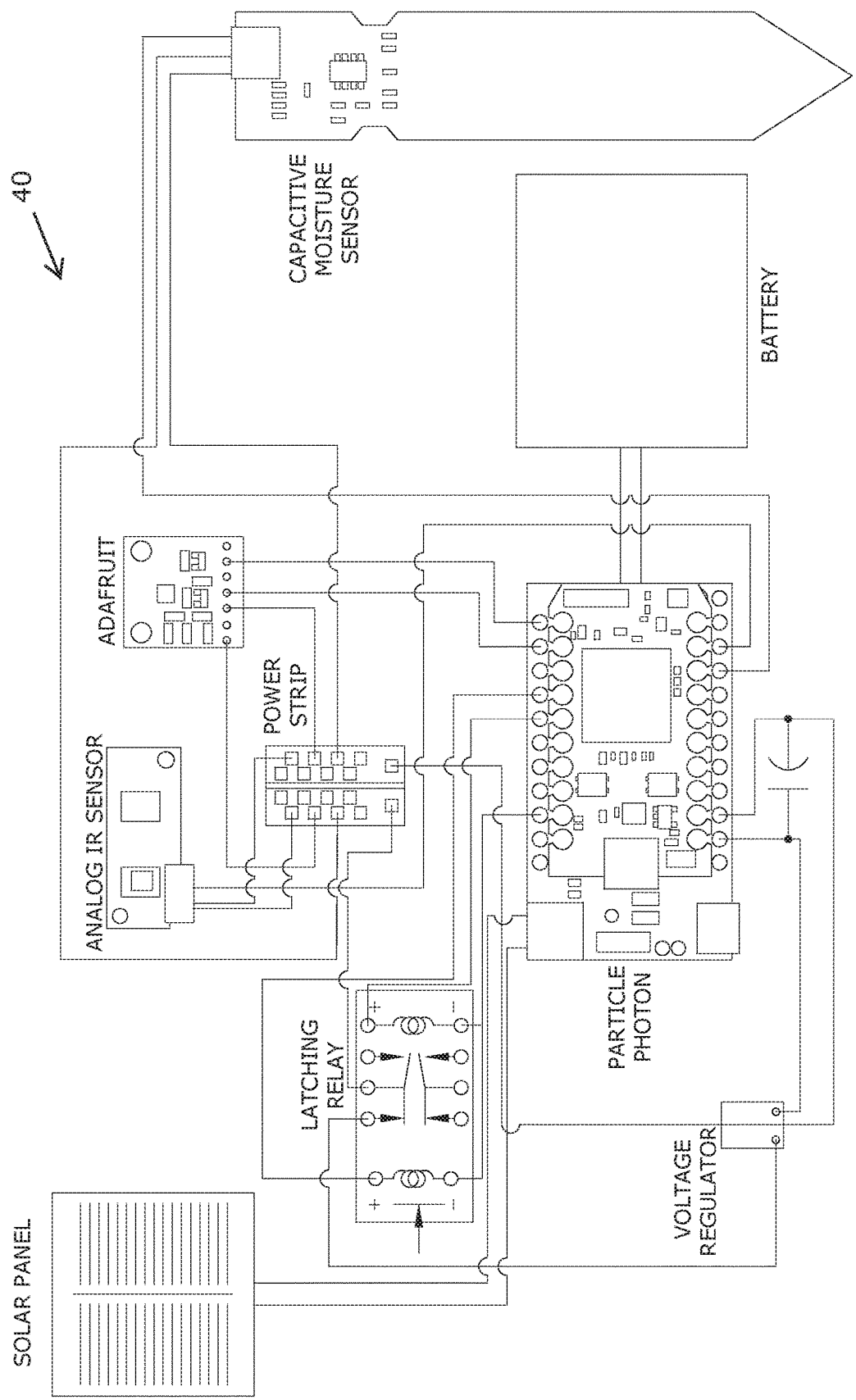
FIG. 6 is a schematic view of an exemplary embodiment of the present invention, illustrating a control circuitry.

Referring now to FIGS. 1 through 6, the present invention may include at least one computing device with a user interface. The computing device may include at least one processing unit coupled to a form of memory. The computing device may include, but not limited to, a microprocessor, a server, a control circuitry, a desktop, laptop, and smart device, such as, a tablet and smart phone. The computing device includes a program product including a machinereadable program code for causing, when executed, the computing device to perform steps. The program product may include software which may either be loaded onto the computing device or accessed by the computing device. The loaded software may include an application on a smart device. The software may be accessed by the computing device using a web browser. The computing device may access the software via the web browser using the internet, extranet, intranet, host server, internet cloud and the like.

The present invention may include a smart lawn sensor 24 adapted to be inserted in a supporting surface 56 (e.g., soil) so as to be among and adjacent to the grass 26 it monitors. The smart lawn sensor 24 may include a moisture sensor comprising a housing 14 and an elongated element 16 for penetrating the supporting surface 56. The elongated element 16 may provide a distal spike for facilitating penetrating the soil. The moisture sensor is adapted to determine the moisture content of the soil.

The smart lawn sensor 24 may provide a control circuitry 40 coupled to a grass height sensor 18 and a temperature-pressure sensor 20, all of which may be disposed within a first housing 22. The first housing 22 may provide a downward-facing portion 50 and an upward-facing portion 52. The grass height sensor 18 may be disposed along the downward-facing portion 50 so as to operatively associate with the grass 26 thereunder. The grass height sensor 18 may utilize infrared technology, such as sharp analog or infrared sensory data capture functionality, ultrasonic measurement devices, electromagnetic imaging functionality or equivalent imaging technology adapted to determined if the grass 26 has reached a predetermined elevation above the supporting surface 56 (or distance relative to the grass height sensor 18), which would be indicative of the need for mowing or other lawn services.

The upward-facing portion 52 may provide a solar energy collector 10 adapted to convert sunlight into power for the control circuitry 40.

It should be understood by those skilled in the art that the use of directional terms such as upwardly, downwardly, and the like are used in relation to the illustrative embodiments as they are depicted in the figures, the upwardly direction (or upper) being toward the top of the corresponding figures and a downwardly direction being toward the bottom of the corresponding figure.

The moisture sensor may be operatively associated with the control circuitry 40. A post 12 may interconnect the moisture sensor and the first housing 22. It should be understood that portions of the smart lawn sensor 24 may be modular, as opposed to a singular, unitary structure, yet work as disclosed herein. For example, the moisture sensor may be physically separated from the grass height sensor 18 wherein the moisture sensor is inserted in the soil, while the grass height sensor 18 is connected to a structure (such as a wall or building) yet still adjacent to the grass 26 it monitors, while all the components are operatively associated wirelessly.

The temperature-pressure sensor 20 is adapted to determine the ambient temperature and pressure. As such, the temperature-pressure sensor 20 may also be dispose along any portion of the first housing 22 or even physically separated from the first housing 22, as long as the temperature-pressure sensor 20 is operatively associated (for example, wirelessly) with the control circuitry 40.

The control circuitry 40 may be adapted to process the sensed data of the grass height sensor 18, the moisture sensor, and/or the temperature-pressure sensor 20 and make a lawn service determination for the need for the grass 26 to be mowed. Typically, the lawn service determination would be automatic if certain pre-selected threshold(s) were met, each threshold being a function of the grass height, moisture content of the soil, the ambient temperature and atmospheric pressure, and/or a combination thereof. Said lawn service determinations and/or their relationship with the pre-selected threshold(s) may be exported via the control circuitry 40 to a remote computing device, such as a mobile phone of the user 28 or the that of a lawn care center 30.

A method of using the present invention may include the following. The smart lawn sensor 24 disclosed above may be provided. A user may insert the smart lawn sensor 24 into the supporting surface covered with grass 26 they want monitored. The insertion distance may be governed by the pre-selected thresholds, for example so that the grass height sensor 18 is at a predetermined elevation about the ground surface so that the "grass height" may be accurately sensed by the grass height sensor 18.

Through a user interface of the user's computing device 28 the user may set a pre-selected grass height that triggers a request for lawn service from the lawn care center 30. The software application in turn talks to the grass height sensor 18 and based on the user's pre-programmed preferences once the grass 26 or weeds reach a pre-selected elevation relative to the supporting surface 56. Once the pre-selected elevation is reached, the control circuitry 40 may be adapted to automatically send a lawn care request to lawn care professionals 30. The software application may also be integrated with a smart home and sprinkler systems. The present invention may be also adapted to monitor the height of crops for irrigation purposes.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A smart lawn sensor, comprising:
   a first housing having an upward-facing surface and a downward-facing surface;
   a grass height sensor disposed in the first housing, so as to be operatively associated with a portion of the downward-facing surface, wherein the grass height sensor is configured to measure a first distance and a second distance between the downward-facing surface and a supporting surface and between the downward-facing surface and an upper elevation of plant life between the supporting surface and the downward-facing surface, respectively;
   a post extending from the downward-facing surface so as to connect the downward-facing surface to the supporting surface;
   a control circuitry coupled to the grass height sensor, wherein the control circuitry is configured to determine a difference between said first and second distances; and
   a moisture sensor integrated with a distal end of the post, so that the moisture sensor measures a moisture content of the supporting surface,
   wherein the control circuitry is configured to programmably set a predetermine difference threshold as a function of the moisture content, wherein the control circuitry is configured to send an alert if the predetermine difference threshold is met or exceeded by said difference.

2. The smart lawn sensor of claim 1, wherein the grass height sensor utilizes infrared imaging functionality to determine said first and second distances.

3. The smart lawn sensor of claim 1, further comprising a solar energy collector integrated with the upward-facing surface, wherein the solar energy collectors converts sunlight to electricity powering the control circuitry.

4. The smart lawn sensor of claim 1, further comprising a temperature and pressure sensor housed in the first housing, where in the temperature and pressure sensor is configured to measure the ambient temperature and atmospheric pressure.

5. A smart lawn sensor comprising:
   a first housing having an upward-facing surface and a downward-facing surface;
   a grass height sensor disposed in the first housing so as to be operatively associated with a portion of the downward-facing surface, wherein the grass height sensor is configured to measure a first distance and a second distance between the downward-facing surface and a supporting surface and between the downward-facing surface and an upper elevation of plant life between the supporting surface and the downward-facing surface, respectively;
   a post extending from the downward-facing surface so as to connect the downward-facing surface to the supporting surface;
   a control circuitry coupled to the grass height sensor, wherein the control circuitry is configured to determine a difference between said first and second distances;
   a temperature and pressure sensor housed in the first housing, where in the temperature and pressure sensor is configured to measure an ambient temperature and atmospheric pressure; and
   a moisture sensor integrated with a distal end of the post, so that the moisture sensor measures a moisture content of the supporting surface, wherein the control circuitry is configured to programmably set a predetermine difference threshold as a function of said difference, the moisture content and the ambient temperature and or the atmospheric pressure, wherein the control circuitry is configured to send an alert if the predetermine difference threshold is met or exceeded by said difference.

6. A smart lawn sensor, comprising:
   a first housing having an upward-facing surface and a downward-facing surface;
   a grass height sensor disposed in the first housing so as to be operatively associated with a portion of the downward-facing surface, wherein the grass height sensor is configured to measure a first distance and a second distance between the downward-facing surface and a supporting surface and between the downward-facing surface and an upper elevation of plant life between the supporting surface and the downward-facing surface, respectively, wherein the grass height sensor utilizes infrared imaging functionality to determine said first and second distances;
   a post extending from the downward-facing surface so as to connect the downward-facing surface to the supporting surface;
   a control circuitry coupled to the grass height sensor, wherein the control circuitry is configured to determine a difference between said first and second distances; and
   a moisture sensor integrated with a distal end of the post, so that the moisture sensor measures a moisture content of the supporting surface;
   a solar energy collector integrated with the upward-facing surface, wherein the solar energy collectors converts sunlight to electricity powering the control circuitry; and
   a temperature and pressure sensor housed in the first housing, wherein the temperature and pressure sensor is configured to measure an ambient temperature and atmospheric pressure, wherein the control circuitry is configured to programmably set a predetermine difference threshold as a function of the moisture content and the ambient temperature and or the atmospheric pressure, wherein the control circuitry is configured to send an alert if the predetermine difference threshold is met or exceeded by said difference.

* * * * *